(12) United States Patent
Beck et al.

(10) Patent No.: US 11,318,178 B2
(45) Date of Patent: May 3, 2022

(54) LACTOBACILLUS REUTERI ATG-F4 STRAIN HAVING FUNCTION OF ENHANCING DOPAMINE SECRETION AND PHARMACEUTICAL COMPOSITION COMPRISING SAME FOR PREVENTION OR TREATMENT OF PSYCHOPATHY

(71) Applicant: ATOGEN CO., LTD, Daejeon (KR)

(72) Inventors: Bo Ram Beck, Daejeon (KR); Ji Hee Kang, Daejeon (KR); Gun Seok Park, Daejeon (KR); Sung Hoon Im, Daejeon (KR); Do Yeun Jeong, Daejeon (KR); Yong Hyun Lee, Daejeon (KR)

(73) Assignee: ATOGEN CO., LTD, Daejeon (KR)

( * ) Notice: Subject to any disclaimer, the term of this patent is extended or adjusted under 35 U.S.C. 154(b) by 0 days.

(21) Appl. No.: 17/050,971

(22) PCT Filed: Jun. 10, 2019

(86) PCT No.: PCT/KR2019/006937
§ 371 (c)(1),
(2) Date: Oct. 27, 2020

(87) PCT Pub. No.: WO2020/116733
PCT Pub. Date: Jun. 11, 2020

(65) Prior Publication Data
US 2021/0228658 A1 Jul. 29, 2021

(30) Foreign Application Priority Data
Dec. 7, 2018 (KR) ........................ 10-2018-0157055

(51) Int. Cl.
*A61K 35/747* (2015.01)
*A23L 33/135* (2016.01)

(52) U.S. Cl.
CPC .......... *A61K 35/747* (2013.01); *A23L 33/135* (2016.08)

(58) Field of Classification Search
None
See application file for complete search history.

(56) References Cited

FOREIGN PATENT DOCUMENTS

| KR | 10-0942290 B1 | 2/2010 |
|---|---|---|
| KR | 10-1799830 B1 | 11/2017 |
| KR | 10-2018-0019474 A | 2/2018 |
| KR | 10-2018-0060928 A | 6/2018 |
| KR | 10-1951919 B1 | 2/2019 |
| WO | 2017/047962 A1 | 3/2017 |

OTHER PUBLICATIONS

Davidson, J. (Science Friday.Apr. 9, 2014 https://www.sciencefriday.com/articles/yogurt-breakfast-of-champions/).*
Mu et al (Frontiers in Microbio. 9(757): 1-8. Apr. 19, 2018).*
Marin et al (Scientific Reports. Mar. 7, 2017. 7:43589, pp. 1-10).*
Hou et al (J. Animal Sci. and Biotech. 2015. 6(14): 1-8).*
John F. Cryan et al., "Mind-altering microorganisms: the impact of the gut microbiota on brain and behaviour", Nature reviews neuroscience, 2012, pp. 701-712 vol. 13(10).
Timothy G. Dinan et al., "Psychobiotics:A Novel Class of Psychotropic", Society of Biological Psychiatry, 2013, pp. 720-726, vol. 74(10).
Tomothy G. Dinan et al., "The impact of gut microbiota on brain and behaviour: implications for psychiatry", Current Opinion in Clinical Nutrition & Metabolic Care, 2015, pp. 552-558, vol. 18, No. 6.
Thomas C Fung et al., "Interactions between the microbiota, immune and nervous systems in health and disease", Nature neuroscience, Feb. 2017, pp. 145-155, vol. 20, No. 2.
Francesca Pistollato et al., "Role of gut microbiota and nutrients in amyloid formation and pathogenesis of Alzheimer disease", Nutrition reviews, 2016, pp. 624-634, vol. 74(10).
Eoin Barrett et al., "The individual-specific and diverse nature of the preterm infant microbiota", Archives of Disease in Childhood—Fetal and Neonatal Edition, fetalneonatal-2012, 2013, pp. F334-F340 vol. 98.
Tracy A. Baskerville et al., "Dopamine and Oxytocin Interactions Underlying Behaviors: Potential Contributions to Behavioral Disorders", CNS neuroscience & therapeutics, 2010, pp. e92-e123, 16(3).
Desbonnet L. et al., "Microbiota is essential for social development in the mouse", Molecular psychiatry, 2014, pp. 148-148, 19(2).
Katerina V.-A. et al. Why does the microbiome affect behaviour?. Nature Reviews Microbiology, 2018, 9 pages.
EFSA Panel on Additives and Products or Substances Used in Animal Feed (FEEDAP), "Guidance on the assessment of bacterial susceptibility to antimicrobials of human and veterinary importance", European Food Safety Authority (EFSA), EFSA Journal 2012 10(6):2740, 10 pages.
Caroline M. Nievergelt et al., "Suggestive Evidence for Association of the Circadian Genes PERIOD3 and ARNTL With Bipolar Disorder", American Journal of Medical Genetics Part B: Neuropsychiatric Genetics, 2006, pp. 234-241, 141B.
Timo Partonen et al., "Three circadian clock genes Per2, Arntl, and Npas2 contribute to winter depression", Annals of medicine, 2007, pp. 229-238, 39.
E Lauretti et al., "Circadian rhythm dysfunction: a novel environmental risk factor for Parkinson's disease", Molecular psychiatry, 2017, pp. 1-7, 22:280.

(Continued)

Primary Examiner — Jennifer E Graser
(74) Attorney, Agent, or Firm — Sughrue Mion, PLLC

(57) ABSTRACT

A *Lactobacillus reuteri* ATG-F4 strain (Accession number KCTC13717BP) is proposed. The strain has the function of enhancing dopamine secretion, and thus can be used as a pharmaceutical composition or a functional health food for the prevention or amelioration of mental illnesses, such as memory disorder, depressive disorder, generalized anxiety disorder, bipolar disorder, and the like, as well as Parkinson's disease, or can be used as a very effective composition for the improvement of memory or cognitive function. Moreover, the strain exhibits anti-inflammatory efficacy of upregulating the expression of IL-10 (interleukin-10) and inhibiting the generation of nitric oxide (NO) and is not resistant to antibiotics, and can thus be readily applied to a variety of foods having health improvement effects.

3 Claims, 8 Drawing Sheets
Specification includes a Sequence Listing.

(56) References Cited

OTHER PUBLICATIONS

Bana Radwin et al., "The role of dopamine in mood disorders and the associated changes in circadian rhythms and sleep-wake cycle", Brain Research, 2018, 35 pages, Accepted Manuscript.
Getinet Ayano, "Dopamine: Receptors, Functions, Synthesis, Pathways, Locations and Mental Disorders: Review of Literatures", Ayano, J Ment Disord Treat, 2016, pp. 1-4 vol. 2, issue 2.
International Search Report of PCT/KR2019/006937 dated Sep. 20, 2019 [PCT/ISA/210].

* cited by examiner ically characterized by LACTOBACILLUS REUTERI ATG-F4 STRAIN HAVING FUNCTION OF ENHANCING DOPAMINE SECRETION AND PHARMACEUTICAL COMPOSITION COMPRISING SAME FOR PREVENTION OR TREATMENT OF PSYCHOPATHY

CROSS REFERENCE TO RELATED APPLICATIONS

This application is a National Stage of International Application No. PCT/KR2019/006937 filed Jun. 10, 2019, claiming priority based on Korean Patent Application No. 10-2018-0157055 filed Dec. 7, 2018, the entire disclosures of which are incorporated herein by reference.

TECHNICAL FIELD

The present disclosure relates to a *Lactobacillus reuteri* ATG-F4 strain (Accession number: KCTC13717BP) having the function of enhancing dopamine secretion and a composition for the prevention or treatment of mental illness containing the same.

BACKGROUND ART

The gut-brain axis is a theory pertaining to symbiosis between microorganisms and animals based on studies on the correlation between gut microbiota and mental health in recent years (Cryan and Dinan, 2012; Fung et al, 2017). This may affect depression, autism, schizophrenia, and even Parkinson's disease and Alzheimer's disease caused by nerve damage, depending on the composition of existing or newly introduced microorganisms in the gut, pathogenicity, ecological characteristics, immunological characteristics, and the like. The mechanism of pathogenesis that acts on cognitive regions and neurons in the gut-brain axis described above includes, based on gut microbiota dysbiosis, 1) increased blood LPS due to increased permeability and inflammation of the gut (Pistollato et al, 2016), 2) adverse effects on nerves due to elevated blood inflammation indicators and abnormal differentiation of gut immune cells (Fung et al, 2017), 3) neuronal apoptosis caused by the accumulation of malignant proteins in the blood due to the dominance of certain bacteria (Dinan and Cryan, 2015), and the like.

Against this background, probiotic microorganisms that exert positive influence on mental health are referred to as psychotropic probiotics, leading to the concept of psychobiotics, and various studies with the goal of practical application of psychobiotics to improvement of mental health are ongoing (Dinan et al., 2013). In order to alleviate mental illness associated with the gut-brain axis, effects such as 1) inflammation suppression, 2) maintenance and strengthening of neurotransmitters, and 3) changes in the gut microbiota that are beneficial to the health of the host may be required.

Therefore, the inventors of the present disclosure have ascertained that, among useful microorganisms, a new microorganism, namely a *Lactobacillus reuteri* ATG-F4 strain, has the function of enhancing the secretion of dopamine and restoring the production of serotonin, making it possible to treat mental illness or improve mental health using the above strain, thus culminating in the present disclosure.

CITATION LIST

Patent Literature (Patent Document 1) Korean Patent No. 10-0942290 (Title: Anti-hypochondria composition with soy yogurt fermented by kimchi lactic-acid bacteria, Applicant: DUDU-WON CO. Ltd, Registration date: Feb. 5, 2010)

(Patent Document 2) Korean Patent Application Publication No. 10-2018-0060928 (Title: Composition for preventing and treating degenerative brain disease using novel lactic-acid bacteria, Applicant: Wedea Com., Laid-open date: Jun. 7, 2018)

Non-Patent Literature (Non-Patent Document 1) Cryan, J. F., & Dinan, T. G. (2012). Mind-altering microorganisms: the impact of gut microbiota on brain and behaviour. Nature Reviews Neuroscience, 13(10), 701.

(Non-Patent Document 2) Dinan, T. G., Stanton, C., & Cryan, J. F. (2013). Psychobiotics: a novel class of psychotropic. Biological Psychiatry, 74(10), 720-726.

(Non-Patent Document 3) Dinan, T. G., & Cryan, J. F. (2015). The impact of gut microbiota on brain and behaviour: implications for psychiatry. Current Opinions in Clinical Nutrition & Metabolic Care, 18(6), 552-558.

(Non-Patent Document 4) Fung, T. C., Olson, C. A., & Hsiao, E. Y. (2017). Interactions between the microbiota, immune and nervous systems in health and disease. Nature Neuroscience, 20(2), 145.

(Non-Patent Document 5) Pistollato, F., Sumalla Cano, S., Elio, I., Masias Vergara, M., Giampieri, F., & Battino, M. (2016). Role of gut microbiota and nutrients in amyloid formation and pathogenesis of Alzheimer's disease. Nutrition Reviews, 74(10), 624-634.

(Non-Patent Document 6) Barrett, E., Kerr, C., Murphy, K., O'Sullivan, O., Ryan, C. A., Dempsey, E. M., & Ross, R. P. (2013). The individual-specific and diverse nature of the preterm infant microbiota. Archives of Disease in Childhood—Fetal and Neonatal Edition, fetalneonatal-2012.

(Non-Patent Document 7) Baskerville, T. A., & Douglas, A. J. (2010). Dopamine and oxytocin interactions underlying behaviors: potential contributions to behavioral disorders. CNS neuroscience & therapeutics, 16(3), e92-e123.

(Non-Patent Document 8) Desbonnet, L., Clarke, G., Shanahan, F., Dinan, T. G., & Cryan, J. F. (2014). Microbiota is essential for social development in the mouse. Molecular psychiatry, 19(2), 146.

(Non-Patent Document 9) Dinan, T. G., & Cryan, J. F. (2015). The impact of gut microbiota on brain and behaviour: implications for psychiatry. Current Opinion in Clinical Nutrition & Metabolic Care, 18(6), 552-558.

(Non-Patent Document 10) Fung, T. C., Olson, C. A., & Hsiao, E. Y. (2017). Interactions between the microbiota, immune and nervous systems in health and disease. Nature Neuroscience, 20(2), 145.

(Non-Patent Document 11) Johnson, K. V. A., & Foster, K. R. (2018). Why does the microbiome affect behaviour? Nature Reviews Microbiology, 1.

(Non-Patent Document 12) EFSA Panel on Additives and Products or Substances used in Animal Feed (FEEDAP). 2012. Guidance on the assessment of bacterial susceptibility to antimicrobials of human and veterinary importance. EFSA Journal 10(6):2740.

(Non-Patent Document 13) Nievergelt C. M., Kripke D. F., Barrett T. B., Burg E., Remick R. A., Sadovnick A. D., McElroy S. L., Keck Jr. P. E., Schork N. J., Kelsoe J. R.: Suggestive evidence for association of the circadian genes PERIOD3 and ARNTL with bipolar disorder. American Journal of Medical Genetics Part B: Neuropsychiatric Genetics 2006, 141:234-241.

(Non-Patent Document 14) Partonen T., Treutlein J., Alpman A., Frank J., Johansson C., Depner M., Aron L., Rietschel M., Wellek S., Soronen P.: Three circadian clock genes Per2, Arntl, and Npas2 contribute to winter depression. Annals of Medicine 2007, 39:229-238.

(Non-Patent Document 15) Lauretti E., Di Meco A., Merali S., Pratico D.: Circadian rhythm dysfunction: a novel environmental risk factor for Parkinson's disease. Molecular Psychiatry 2017, 22:280.

(Non-Patent Document 16) Radwan B., Liu H., Chaudhury D.: The role of dopamine in mood disorders and the associated changes in circadian rhythms and sleep-wake cycle. Brain Research 2018.

(Non-Patent Document 17) Ayano G. Dopamine: Receptors, Functions, Synthesis, Pathways, Locations and Mental Disorders: Review of Literatures. Ayano, J. Ment. Disord. Treat. 2016, 2(2), 1-4.

DISCLOSURE

Technical Problem

An objective of the present disclosure is to provide a *Lactobacillus reuteri* ATG-F4 strain (Accession number: KCTC13717BP) having the function of enhancing dopamine secretion and a composition for the prevention or treatment of mental illness containing the same.

Technical Solution

An aspect of the present disclosure provides a *Lactobacillus reuteri* ATG-F4 strain (Accession number: KCTC13717BP) having the function of enhancing dopamine secretion.

Also, the *Lactobacillus reuteri* ATG-F4 strain has anti-inflammatory efficacy.

Another aspect of the present disclosure provides a pharmaceutical composition for preventing or treating mental illness or a functional health food for preventing or ameliorating mental illness, containing the *Lactobacillus reuteri* ATG-F4 strain or a culture thereof, in which the mental illness may be selected from the group consisting of attention deficit hyperactivity disorder, memory disorder, depressive disorder, generalized anxiety disorder, and bipolar disorder.

Since the strain of the present disclosure or a culture thereof is capable of increasing the production of dopamine, it may be provided as a pharmaceutical composition for the prevention or treatment of Parkinson's disease or a functional health food for the prevention or amelioration of Parkinson's disease.

In addition, the strain of the present disclosure or a culture thereof is also easy to use as a functional health food for improving memory or cognitive function due to the activity of increasing dopamine secretion.

The functional health food is preferably selected from the group consisting of drinks, meats, sausages, breads, candies, snacks, noodles, ice creams, dairy products, soups, electrolytic beverages, drinking water, alcoholic beverages, gums, teas, and vitamin complexes.

Hereinafter, a detailed description will be given of the present disclosure.

A *Lactobacillus reuteri* ATG-F4 strain according to the present disclosure has anti-inflammatory efficacy in addition to the function of enhancing dopamine secretion, and is more preferably characterized by upregulating the expression of IL-10 (interleukin-10) and inhibiting the generation of NO (nitric oxide), thus activating the anti-inflammatory function.

The strain of the present disclosure is not resistant to any antibiotic selected from the group consisting of ampicillin, vancomycin, gentamicin, kanamycin, streptomycin, clindamycin, erythromycin, tetracycline and chloramphenicol.

In addition, the present disclosure may provide a pharmaceutical composition containing the *Lactobacillus reuteri* ATG-F4 strain or a culture thereof. The pharmaceutical composition is effective at preventing, ameliorating or treating various mental illnesses, such as attention deficit hyperactivity disorder, memory disorder, depressive disorder, generalized anxiety disorder, bipolar disorder, and the like, as well as Parkinson's disease.

The *Lactobacillus reuteri* ATG-F4 strain or a culture thereof may be added in an amount of 0.001 to 100 wt % to the pharmaceutical composition of the present disclosure.

The pharmaceutical composition may be formulated into oral dosage forms, such as powders, granules, tablets, capsules, suspensions, emulsions, syrups, and aerosol formulations, as well as formulations for external use, suppositories, and sterile injection solutions, in accordance with typical individual processes. A carrier, an excipient and a diluent that may be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. The formulation may be typically prepared using a diluent or excipient such as a filler, an extender, a binder, a wetting agent, a disintegrant, a surfactant, and the like. A solid formulation for oral administration may include tablets, pills, powders, granules, capsules, and the like, and such a solid formulation may be prepared by mixing the strain of the present disclosure or a culture thereof with at least one excipient, for example, starch, calcium carbonate, sucrose, lactose, gelatin, and the like. In addition to a simple excipient, lubricants such as magnesium stearate, talc and the like may be used. An oral liquid formulation may include suspensions, solutions, emulsions, syrups, and the like, and may also include not only simple diluents, such as water or liquid paraffin, but also various excipients, for example, wetting agents, sweeteners, fragrances, preservatives, and the like. A formulation for parenteral administration may include sterilized aqueous solutions, non-aqueous solvents, suspensions, emulsions, lyophilized preparations, and suppositories. As non-aqueous solvents or suspension agents, propylene glycol, polyethylene glycol, vegetable oil such as olive oil, injectable esters such as ethyl oleate and the like may be used. As the base of a suppository, Witepsol, Macrogol, Tween 61, cacao butter, laurin fat, glycerogelatin and the like may be used.

The amount of the pharmaceutical composition according to the present disclosure, when administered, may vary depending on the age, gender and weight of the subject to be treated, the particular disease or pathological condition for treatment, the severity of the disease or pathological condition, the administration route, and the judgment of the prescriber. A dose determination based on these factors will be easily made by those skilled in the art, and the dose typically falls in the range of 0.01 mg/kg/day to about 2000 mg/kg/day. Preferably, the dose is set to the range of 1 mg/kg/day to 500 mg/kg/day. The administration may be carried out once a day or several times a day. The dose does not in any way limit the scope of the present disclosure.

The pharmaceutical composition of the present disclosure may be administered to mammals such as mice, livestock, humans, and the like through various routes. All modes of administration may be considered, and the pharmaceutical composition of the present disclosure may be administered, for example, through oral, rectal, intravenous, intramuscular, subcutaneous, intrauterine dural or intracerebrovascular injection. Since the strain of the present disclosure has little toxicity and minimal side effects, it is a drug that may be safely used even when taken for a long time for prophylactic purposes.

In addition, the present disclosure provides a functional health food containing the *Lactobacillus reuteri* ATG-F4 strain or a culture thereof and a food additive acceptable for food.

The functional health food is effective at preventing or ameliorating various mental illnesses such as memory disorder, depressive disorder, general anxiety disorder, bipolar disorder, and the like, as well as Parkinson's disease, and is also effective at improving memory and cognitive function.

The *Lactobacillus reuteri* ATG-F4 strain or a culture solution thereof may be added in an amount of 0.001 to 100 wt % to the functional health food of the present disclosure. The functional health food of the present disclosure is provided in the form of tablets, capsules, pills or liquids, and examples of the food to which the strain of the present disclosure may be added may include drinks, meats, sausages, breads, candies, snacks, noodles, ice creams, dairy products, soups, electrolytic beverages, drinking water, alcoholic beverages, gums, teas, and vitamin complexes.

The concept of treatment induced by a composition containing the strain of the present disclosure or a culture solution thereof has a broad concept in which a disease is prevented, alleviated, ameliorated, or treated due to ingestion of the strain of the present disclosure or a culture solution thereof.

Advantageous Effects

According to the present disclosure, a *Lactobacillus reuteri* ATG-F4 strain (Accession number: KCTC13717BP) has the function of enhancing dopamine secretion, and thus can be used as a functional health food capable of preventing or ameliorating mental illnesses, such as attention deficit hyperactivity disorder, memory disorder, depressive disorder, generalized anxiety disorder, bipolar disorder, and the like, as well as Parkinson's disease, and can be used as a very effective composition for improving memory or cognitive function. Moreover, the strain described above has anti-inflammatory efficacy of upregulating the expression of IL-10 (interleukin-10) and inhibiting the generation of NO (nitric oxide) and is not resistant to antibiotics, and can thus be readily applied to a variety of foods having health improvement effects.

MODE FOR DISCLOSURE

Figure 1A:
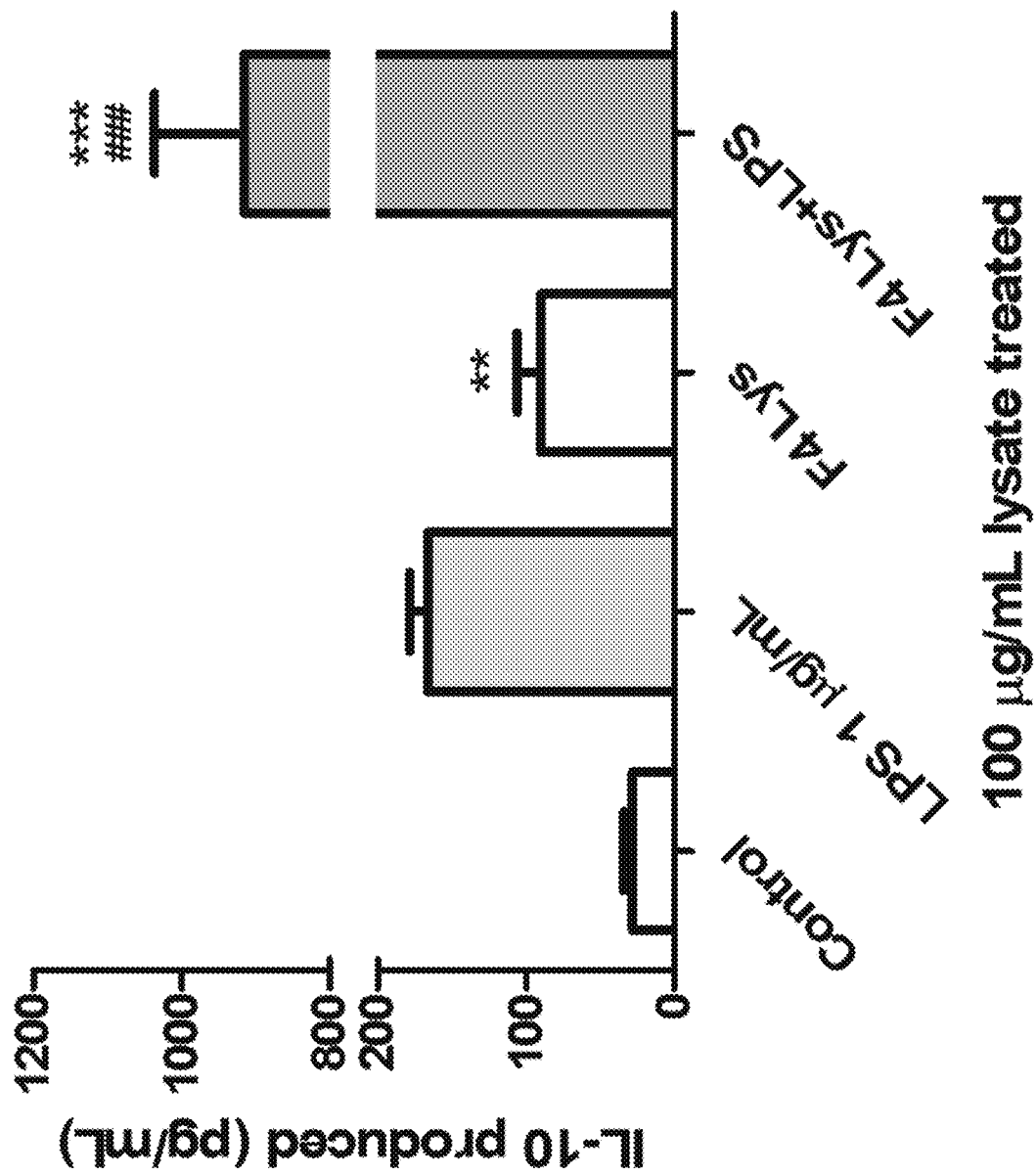
FIGS. 1A and 1B show results showing that the production of IL-10 is increased when inducing inflammation with LPS in RAW 264.7 cells using *Lactobacillus reuteri* ATG-F4 (FIG. 1A) and the results of confirmation of the effect of inhibiting the generation of NO due to the inflammatory response induced by LPS (FIG. 1B)

A better understanding of the present invention will be obtained through the following examples. However, the present invention is not limited to these examples, and may be embodied in other forms. These examples are provided to thoroughly explain the invention and to sufficiently transfer the spirit of the present invention to those skilled in the art.

Example 1. Isolation and Identification of F4 Lactic-Acid Bacteria

Neonatal feces (donor: Baek * Hyun, born May 23, 2018, Daejeon, Korea) was donated on May 31, 2018 ($8^{th}$ day after birth), and the resulting product obtained by diluting neonatal feces in 0.9% saline using a 10-fold serial dilution method was spread on a de Man-Rogosa-Sharpe (MRS) medium and cultured at 37° C. for about 48 hr.

The colonies of lactic-acid bacteria that formed in the cultured MRS medium were observed using a microscope, and lactic-acid bacteria of the *bacillus* type that did not exhibit a catalase reaction were selected, subjected to whole-genome sequencing, and named F4.

The 16S rRNA sequencing of the F4 strain was performed by Solgent (Daejeon). Using 27F (5'-AGA GTT TGA TCC TGG CTC AG-3'; SEQ ID NO: 2), 518F (5'-CCA GCA GCC GCG GTA ATA C-3'; SEQ ID NO: 3), 907R (5'-CCG TCA ATT CMT TTR AGT TT-3'; SEQ ID NO: 4), and 1492R (5'-GGT TAC CTT GTT ACG ACT T-3'; SEQ ID NO: 5) as primers for sequencing, nucleotide sequence reading was performed a total of four times, and the contigs obtained through nucleotide sequence alignment of each reading were analyzed using a BLAST online tool (https://blast.ncbi.nlm.nih.gov/Blast.cgi) of the National Center for Biotechnology Information (NCBI).

Based on the results of comparison of the nucleotide sequence of SEQ ID NO: 1 obtained through 16S rRNA sequencing with the BLAST database of NCBI, the 16S rRNA sequence thereof was 99.9% identical to that of a *Lactobacillus reuteri* strain IRT, indicating that the taxonomic position thereof belongs to *Lactobacillus reuteri*.

Accordingly, the strain of the present disclosure was named *Lactobacillus reuteri* ATG-F4 and deposited with the Korean Collection for Type Cultures on Nov. 15, 2018 (Accession number: KCTC13717BP).

SEQ ID NO: 1: 16S rRNA Sequence of *Lactobacillus reuteri* ATG-F4

TCAGGATGAACGCCGGCGGTGTGCCTAATACATGCAAGTCGTACGCACT

GGCCCAACTGATTGATGGTGCTTGCACCTGATTGACGATGGATCACCAG

TGAGTGGCGGACGGGTGAGTAACACGTAGGTAACCTGCCCCGGAGCGGG

GGATAACATTTGGAAACAGATGCTAATACCGCATAACAACAAAAGCCGC

ATGGCTTTTGTTTGAAAGATGGCTTTGGCTATCACTCTGGGATGGACCT

GCGGTGCATTAGCTAGTTGGTAAGGTAACGGCTTACCAAGGCGATGATG

CATAGCCGAGTTGAGAGACTGATCGGCCACAATGGAACTGAGACACGGT

CCATACTCCTACGGGAGGCAGCAGTAGGGAATCTTCCACAATGGGCGCA

AGCCTGATGGAGCAACACCGCGTGAGTGAAGAAGGGTTTCGGCTCGTAA

AGCTCTGTTGTTGGAGAAGAACGTGCGTGAGAGTAACTGTTCACGCAGT

GACGGTATCCAACCAGAAAGTCACGGCTAACTACGTGCCAGCAGCCGCG

GTAATACGTAGGTGGCAAGCGTTATCCGGATTTATTGGGCGTAAAGCGA

GCGCAGGCGGTTGCTTAGGTCTGATGTGAAAGCCTTCGGCTTAACCGAA

GAAGTGCATCGGAAACCGGGCGACTTGAGTGCAGAAGAGGACAGTGGAA

CTCCATGTGTAGCGGTGGAATGCGTAGATATATGGAAGAACACCAGTGG

CGAAGGCGGCTGTCTGGTCTGCAACTGACGCTGAGGCTCGAAAGCATGG

GTAGCGAACAGGATTAGATACCCTGGTAGTCCATGCCGTAAACGATGAG

TGCTAGGTGTTGGAGGGTTTCCGCCCTTCAGTGCCGGAGCTAACGCATT

AAGCACTCCGCCTGGGGAGTACGACCGCAAGGTTGAAACTCAAAGGAAT

TGACGGGGGCCCGCACAAGCGGTGGAGCATGTGGTTTAATTCGAAGCTA

CGCGAAGAACCTTACCAGGTCTTGACATCTTGCGCTAACCTTAGAGATA

AGGCGTTCCCTTCGGGGACGCAATGACAGGTGGTGCATGGTCGTCGTCA

GCTCGTGTCGTGAGATGTTGGGTTAAGTCCCGCAACGAGCGCAACCCTT

GTTACTAGTTGCCAGCATTGAGTTGGGCACTCTAGTGAGACTGCCGGTG

ACAAACCGGAGGAAGGTGGGGACGACGTCAGATCATCATGCCCCTTATG

ACCTGGGCTACACACGTGCTACAATGGACGGTACAACGAGTCGCAAACT

CGCGAGAGTAAGCTAATCTCTTAAAGCCGTTCTCAGTTCGGACTGTAGG

CTGCAACTCGCCTACACGAAGTCGGAATCGCTAGTAATCGCGGATCAGC

ATGCCGCGGTGAATACGTTCCCGGGCCTTGTACACACCGCCCGTCACAC

CATGGGAGTTTGTAACGCCCAAAGTCGGTGGCCTAACCTTTATGGAGGG

AGCCGCCTAAGGCGGGACAGATGACTGGGGTGAAGTCGTAACAGGAAAC

CCCG

In addition, an API50 CH test (BioMerieux, France) was performed in order to investigate identification and characteristics through a sugar fermentation pattern. Briefly, lactic-acid bacteria that were cultured to purity in 10 ml of an API 50CHL medium (BioMerieux, France) were suspended until an absorbance $OD_{600}$ of about 0.5 was obtained, after which the culture suspension was inoculated into each cupule of an API 50CH test strip and cultured at 37° C. The results of sugar fermentation were confirmed 24, 48, and 72 hr after inoculation, and are shown in Table 1 below.

TABLE 1

| Carbohydrates | Lb. reuteri ATG-F4 |
|---|---|
| Glycerol | − |
| Erythritol | − |
| D-Arabinose | W |
| L-Arabinose | + |
| Ribose | + |
| D-Xylose | W |
| L-Xylose | − |
| Adonitol | W |
| Methyl-βD-xylopyranoside | − |
| Galactose | + |
| Glucose | + |
| Fructose | − |
| Mannose | − |
| Sorbose | − |
| Rhamnose | W |
| Dulcitol | − |
| Inositol | W |
| Mannitol | − |
| Sorbitol | W |
| Methyl-αD-mannopyranoside | − |
| Methyl-αD-Glucopyranoside | W |
| N-Acetylglucosamine | − |
| Amygdalin | − |
| Arbutin | W |
| Esculin | + |
| Salicin | W |
| Cellobiose | W |
| Maltose | + |
| Lactose | + |
| Melibiose | + |
| Sucrose | + |
| Trehalose | − |
| Inulin | − |
| Melezitose | − |
| Raffinose | + |
| Starch | − |
| Glycogen | − |
| Xylitol | − |
| Gentiobiose | W |
| Turanose | − |
| Lyxose | − |
| Tagatose | − |
| D-Fucose | − |
| L-Fucose | + |
| D-Arabitol | W |
| L-Arabitol | W |
| Gluconate | + |
| 2-keto-gluconate | − |
| 5-keto-gluconate | − |

Positive: +, weak positive: w, negative: −

Based on the results of investigation of sugar degradation capability of F4 lactic-acid bacteria, a weak positive response (blue turns to green within 48 hr) was observed for D-arabinose, D-xylose, adonitol, rhamnose, inositol, sorbitol, methyl-αD-glucopyranoside, arbutin, salicin, cellobiose, gentiobiose, L-arabitol, and D-arabitol, and a positive response (blue turns to yellow within 48 hr) was observed for L-arabinose, ribose, galactose, glucose, esculin, maltose, lactose, melibiose, sucrose, raffinose, L-fucose and gluconate. The ability thereof to degrade a total of 25 sugars was exhibited.

Example 2. Antibiotic Safety of F4 Lactic-Acid Bacteria

The antibiotic test was performed using E-test strips of nine types of antibiotics (BioMerieux, France) including ampicillin, vancomycin, gentamicin, kanamycin, streptomycin, clindamycin, erythromycin, tetracycline, and chloramphenicol to determine the minimum inhibitory concentration (MIC). Briefly, lactic-acid bacteria to be tested were each suspended to an absorbance $OD_{600}$ of about 0.8 and were then spread on an MRS solid medium using a sterile cotton swab. The solid medium on which the lactic-acid bacteria were spread was dried for about 3 min, and the E-test strip was placed thereon, followed by culture at 37° C. for about 24-48 hr. Here, due to the nature of lactic-acid bacteria, intrinsic resistance to gentamicin, kanamycin, and streptomycin, which are aminoglycosides, may occur, and thus, as a test medium for the corresponding antibiotics, a platecount agar (PCA, Difco Laboratories, USA) or a Mueller-Hinton agar (MHA, Difco Laboratories, USA) was used. For the types of antibiotics and the criteria for the minimum inhibitory concentration that can be considered safe, reference was made to guidelines published by the European Food Safety Authority (EFSA) (EFSA Panel on Additives and Products or Substances used in Animal Feed, 2012).

Table 2 below shows experimental results of measuring the minimum inhibitory concentration (MIC) of *Lactobacillus reuteri* ATG-F4 lactic-acid bacteria on major antibiotics, in which the limit values suggested by each EFSA are recorded together. As a result, antibiotic sensitivity significantly lower than the limits in EFSA guidelines was observed, and there was no risk of exchanging genes having antibiotic resistance.

Moreover, even when predicting the pathogenicity of F4 lactic-acid bacteria through PathoFinder using whole-genome information, as will be described later, it was confirmed that the F4 lactic-acid bacteria were a non-human pathogen based on the results of comparison with the database and were thus harmless to the human body (Example 6).

100 ng/ml, an inflammation induction experimental group treated both with 1 μg/ml of lipopolysaccharide (LPS, Sigma-Aldrich, Germany) and with F4 lactic-acid bacteria lysate, an experimental group treated with 1 μg/ml of LPS as a positive control, and an experimental group not treated with any material as a negative control. The cells were cultured at 37° C. and 5% $CO_2$ for 24 hr after material treatment, and the cell culture solution was recovered, followed by enzyme-linked immunosorbent assay (ELISA) for anti-inflammatory cytokine IL-10 using a mouse IL-10 Quantikine ELISA Kit (R&D systems, USA). In order to confirm whether the generation of nitric oxide (NO) as an additional inflammation indicator was inhibited in the LPS-induced group, a predetermined amount of the cell culture supernatant obtained in the cell experiment for measuring cytokines was transferred into 96 wells, and 100 μl of a Griess reagent (modified, SIGMA, USA) was injected thereto, after which reaction was carried out at room temperature for 10 min and absorbance at 540 nm was measured using an ELISA reader. The amount of NO that was produced was calculated by comparing the proportion of NO present in the cell culture solution with the LPS-treated group as a control.

Figure 1B:
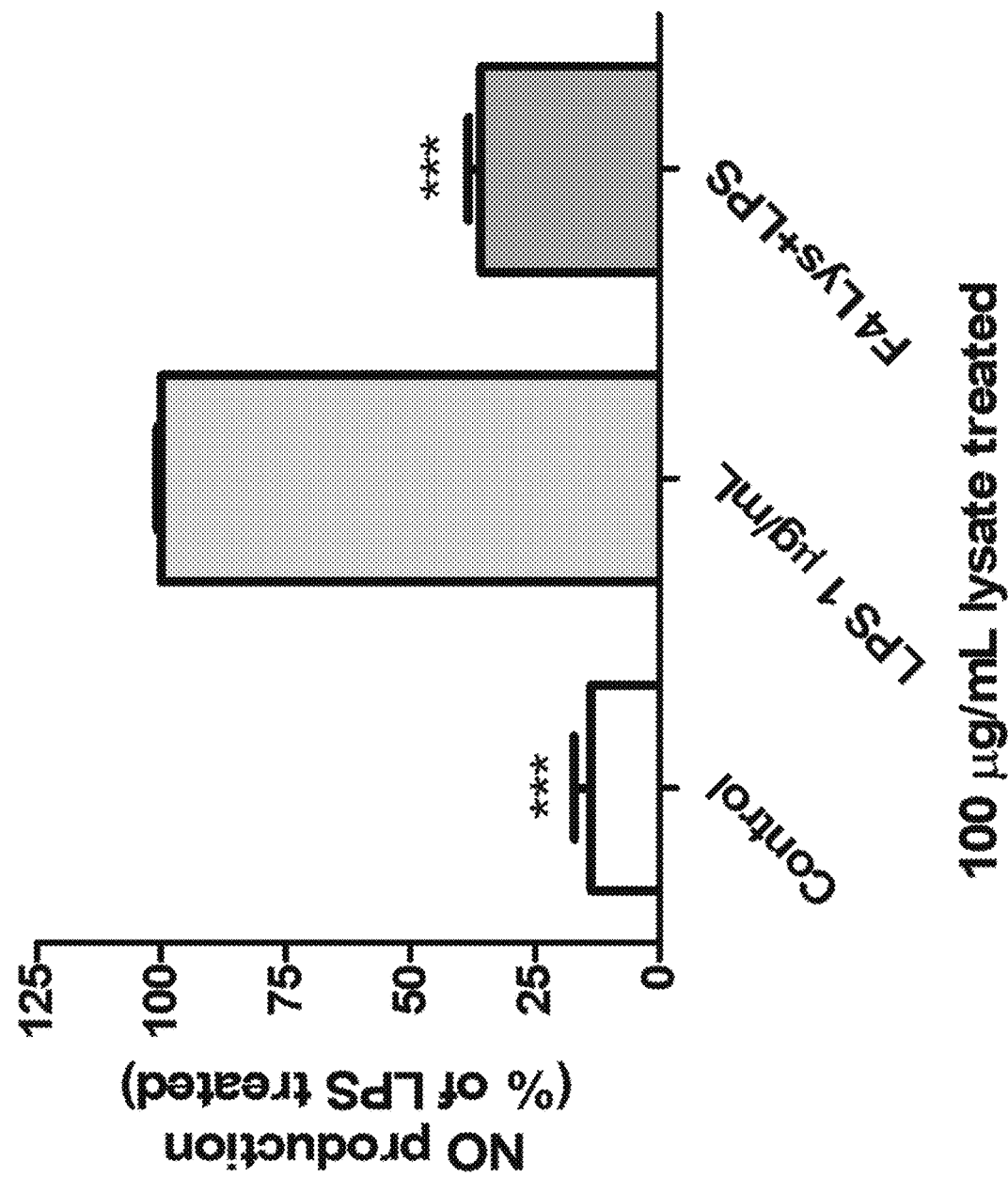

As a result, as shown in FIGS. 1A and 1B, when RAW 264.7 was treated with the F4 lactic-acid bacteria lysate alone, IL-10 was produced in an amount of 90.38 pg/ml and was thus regarded as significantly induced, compared to 28.24 pg/ml, which was the production of IL-10 of the control without any treatment (FIG. 1A). When the LPS inflammatory response was induced, IL-10 was produced in

TABLE 2

| Strains | μg/ml | | | | | | | | |
|---|---|---|---|---|---|---|---|---|---|
| | AMP | VAN | GEN | KAN | STR | CD | ERY | TET | CM |
| Lb. reuteri ATG-F4 | 0.25 | NR | 0.5 | 3 | 0.38 | 0.016 | 0.64 | 0.75 | 1.5 |
| EFSA guideline | 4 | NR | 8 | 64 | 64 | 1 | 1 | 16 | 4 |

AMP, ampicillin; VAN, vancomycin; GEN, gentamicin; KAN, kanamycin; STR, Streptomycin; CD, clindamycin; ERY, erythromycin; TET, tetracycline; CM, Chloramphenicol; NR, not required.

Example 3. Confirmation of Anti-Inflammatory Effect of F4 Lactic-Acid Bacteria

In order to measure the anti-inflammatory effect of F4 lactic-acid bacteria, a cytokine quantification experiment using cells was performed. F4 lactic-acid bacteria as a treatment material were subjected to liquid culture in an MRS broth and were then centrifuged, after which the cells of the strain were recovered and concentrated 10-fold. The concentrated solution thus obtained was treated with lysozyme for 1 hr, lysed through sonication, and then quantified through solid content analysis. The cells that were used were a mouse macrophage cell line RAW264.7, and the medium used for each cell experiment was a Gibco® Dulbecco's Modified Eagle Medium (DMEM, Gibco, USA) supplemented with 10% fetal bovine serum (Gibco, USA) and 1% penicillin/streptomycin cocktail (Sigma-Aldrich, Germany). RAW264.7 cells cultured at about 80-90% confluency before material treatment were recovered and seeded in an amount of $1 \times 10^6$ cells per well of a 24-well plate. After seeding, culture was carried out in an environment of 37° C. and 5% $CO_2$ for 24 hr in order to realize attachment to the 24-well plate and stabilization thereof. The experimental groups that were used were an experimental group treated with F4 lactic-acid bacteria lysate alone at a concentration of an amount of 166.60 pg/ml, and when the F4 lactic-acid bacteria lysate was simultaneously added, IL-10 was produced in an amount of 916.39 pg/ml, which was about 5.5 times as high. It can be seen that, as a substantial effect of inhibiting inflammation by the anti-inflammatory cytokine IL-10, the NO production also significantly reduced LPS-induced inflammation to a level of 35.89% (FIG. 1B).

Example 4. Effect of F4 Lactic-Acid Bacteria on Inducing Neurotransmitter in Blood Before all animal experiments, animal experimentation was approved and approval number ATG-IACUC-REV-180810 was granted through appropriate procedures by the Institutional Animal Care and Use Committee (IACUC) of AtoGEN, and a guide to ethical animal experiments was followed. 4-week-old C57BL/6J mice were purchased through Central Laboratory Animal (Seoul, Korea), and the experimental groups that were used were a control fed with general feed and drinking water (Ctrl), a gut microbiota dysbiosis experimental group (Amp) fed with general feed and drinking water containing 1 g/l of ampicillin, and an experimental group fed with general feed and drinking water containing about $10^7$ CFU/ml of lactic-acid bacteria F4 (F4). Five mice were used for each experimental group. After stabilizing the 4-week-old mice for 1 week, the experiment was conducted for 4 weeks using the experimental groups described above. The entire experiment was independently repeated twice.

After the 4-week feeding experiment, the mice were anesthetized using ether, and blood was obtained from the heart thereof. The blood thus obtained was allowed to harden at room temperature for 1 hr, and was then centrifuged at 2,500 rpm for 20 min to obtain serum. The serum thus obtained was measured to determine the amounts of dopamine and serotonin in the blood using a dopamine ELISA kit (Abnova, Taiwan) and a serotonin ELISA kit (Abcam, USA).

Figure 2A:
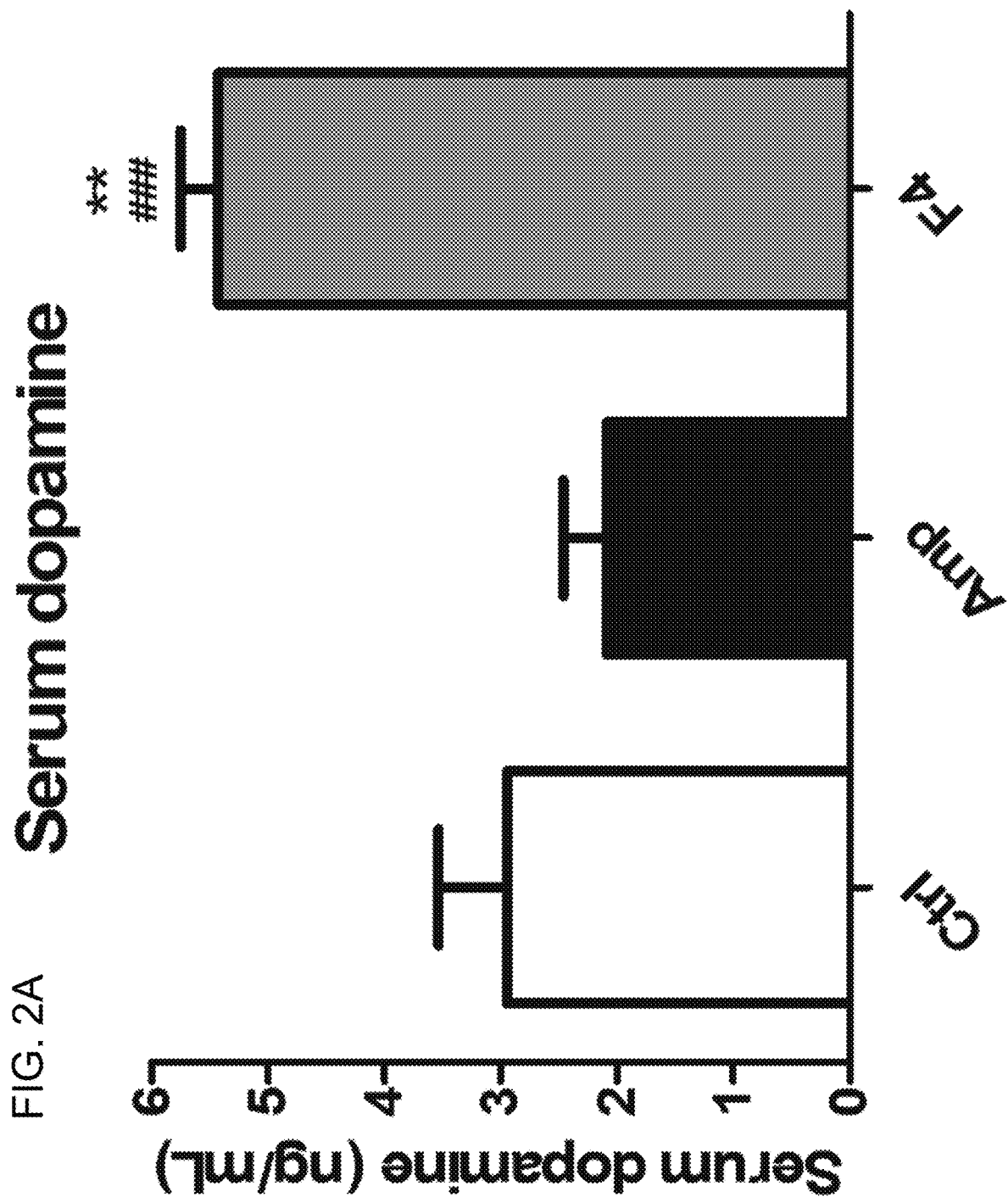
FIGS. 2A and 2B show the dopamine concentration (FIG. 2A) increased in the serum and the maintenance of serotonin in the serum (FIG. 2B) in mice administered with *Lactobacillus reuteri* ATG-F4 or ampicillin (Amp) for 4 weeks.
Figure 2B:
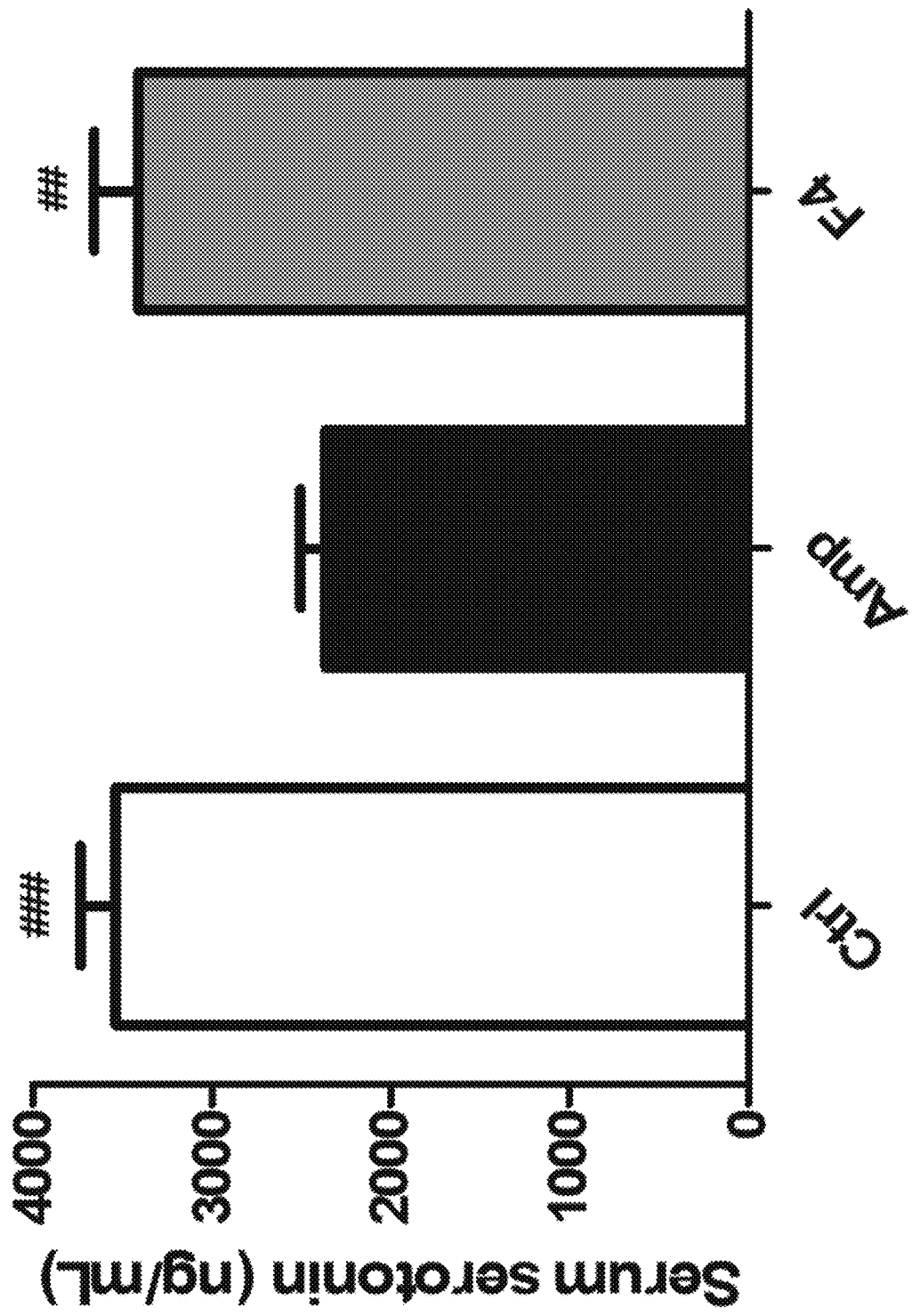

As a result of analyzing the serum of each experimental mouse recovered at the end of the experiment, as shown in FIGS. 2A and 2B, it was confirmed that dopamine was produced in amounts of 2.95 ng/ml in the control (Ctrl), 2.09 ng/ml in the gut microbiota dysbiosis group (Amp), and 5.43 ng/ml in the group fed with F4 lactic-acid bacteria (F4), based on which there was no significant difference between Ctrl and Amp, but in F4, the production of dopamine was significantly increased by about 3 times compared to Ctrl and Amp (FIG. 2A). Also, the amount of serotonin was measured to be 3537.2 ng/ml in Ctrl, 2365.0 ng/ml in Amp, and 3413.3 ng/ml in F4, based on which there was no difference between Ctrl and F4, which were found to be significantly high compared to the group fed with antibiotic (FIG. 2B). It was confirmed that the amount of serotonin was significantly reduced compared to Ctrl and F4 due to the gut microbiota dysbiosis in Amp.

Example 5. Changes in Gut Microbiota Induced by F4 Lactic-Acid Bacteria

In the animal experiment performed in Example 4, feces were freshly collected for each individual in each experimental group by placing the mice of each experimental group in a separate cage for 30 min, and were immediately frozen at −80° C. From the metagenomic DNA extracted from the frozen sample, the amplicon sequence of the V3-V4 region of 16S rRNA was obtained using the Miseq platform of Macrogen Inc., and changes in gut microbiota due to F4 lactic-acid bacteria were analyzed therefrom.

Figure 3:
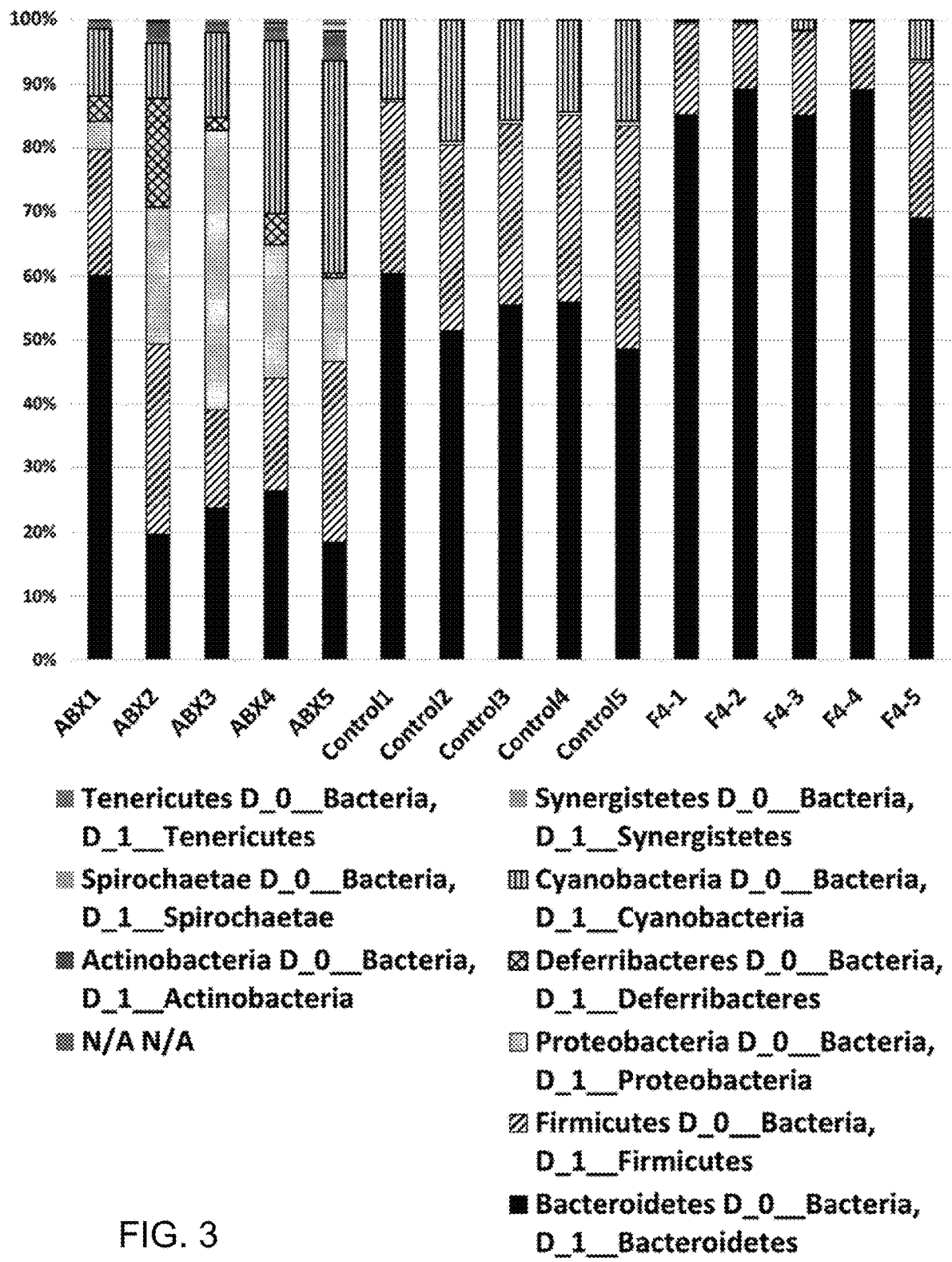
FIG. 3 shows the results of analysis of changes in microbiota of the mouse model depending on the ingestion of *Lactobacillus reuteri* ATG-F4 lactic-acid bacteria (ABX: experimental group treated with antibiotic, Control: untreated experimental group, F4: experimental group fed with F4 lactic-acid bacteria)

As a result, as shown in FIG. 3, in order to compare changes in gut microbiota due to the F4 lactic-acid bacteria, when comparing groups divided into the antibiotic-treated group (ABX, drinking water containing 1 g/l of ampicillin), the untreated group (Control), and the group treated with F4 lactic-acid bacteria (F4) (five mice in each group), it was confirmed that the group treated with the F4 strain significantly increased the amount of Bacteroidetes (light blue) and inhibited the amount of Proteobacteria (purple), thereby exhibiting a probiotic effect of changing gut microbiota. In addition, when compared with the control, noticeable changes in Firmicutes (orange) were observed in all mice fed with F4.

Example 6. Whole-Genome Analysis of F4 Lactic-Acid Bacteria

For whole-genome analysis of F4 lactic-acid bacteria, genomic DNA was extracted, and the nucleotide sequence thereof was analyzed using Pacific Bioscience's Single-Molecule Real-Time (SMRT) sequencing technique. The nucleotide sequence data thus obtained was assembled using the Hierarchical Genome Assembly Process (HAGP) 2 protocol of SMRT analysis software v2.3.0, and Rapid Annotation using a Subsystem Technology (RAST) server (http://rast.nmpdr.org/) was utilized for annotation. In addition, Average Nucleotide Identity (ANI) analysis was performed in order to confirm the similarity to the previously known *Lactobacillus reuteri* strain, and safety was verified once more from genetic information using PathoFinder 1.1 https://cge.cbs.dtu.dk/services/PathogenFinder/).

Based on the results of comparison of the genome information of the F4 lactic-acid bacteria identified in this way with 12 strains of the genus *Lactobacillus reuteri* registered as a complete genome sequence on November 2018, all genome sizes were different, and the results of ANI analysis showed a difference of 0.01-4.66%, indicating that the strain of the present disclosure was a strain independent from the existing strains (Table 3).

TABLE 3

| Strain | Size (Mb) | GC % | ANI | Scaffolds | Release Date |
|---|---|---|---|---|---|
| ATG-F4 | 2.04151 | 38.9 | — | 1 | — |
| DSM 20016 | 1.99962 | 38.9 | 99.99 | 1 | 2007 Jun. 01 |
| JCM 1112 | 2.03941 | 38.9 | 99.98 | 1 | 2008 Apr. 15 |
| SD2112 | 2.31684 | 39 | 95.47 | 5 | 2011 Jun. 20 |
| ATCC 53608 | 2.09124 | 38.8 | 95.87 | 3 | 2015 Nov. 17 |
| I5007 | 2.09328 | 38.9 | 96.34 | 7 | 2013 Jun. 14 |
| TD1 | 2.14545 | 38.8 | 96.46 | 1 | 2013 Jul. 23 |
| IRT | 1.99397 | 38.9 | 99.96 | 1 | 2015 Jul. 06 |
| ZLR003 | 2.2341 | 38.7 | 95.92 | 1 | 2016 Apr. 12 |
| I49 | 2.04477 | 38.8 | 96.47 | 1 | 2016 Jul. 20 |
| Byun-re-01 | 2.24451 | 38.9 | 96.28 | 1 | 2018 Jul. 13 |
| SKKU-OGDONS-01 | 2.25997 | 38.9 | 96.33 | 1 | 2018 Jul. 13 |
| WHH1689 | 2.04418 | 39.3 | 95.34 | 1 | 2018 Apr. 26 |

Also, when categorizing the coding sequence based on the annotated information, it was confirmed that the strain of the present disclosure had 112 genes associated with carbohydrate transport and metabolism and 81 genes associated with cell wall, membrane, and envelope biogenesis, and thus exhibited probiotic efficacy (Table 4).

TABLE 4

| Predicted function | Gene count |
|---|---|
| Translation, ribosomal structure and biogenesis | 138 |
| RNA processing and modification | 0 |
| Transcription | 109 |
| Replication, recombination and repair | 214 |
| Chromatin structure and dynamics | 0 |
| Cell cycle control, cell division, chromosome partitioning | 19 |
| Nuclear structure | 0 |
| Defense mechanisms | 34 |
| Signal transduction mechanisms | 48 |
| Cell wall/membrane/envelope biogenesis | 81 |
| Cell motility | 4 |
| Cytoskeleton | 0 |
| Extracellular structures | 0 |
| Intracellular trafficking, secretion, and vesicular transport | 20 |
| Posttranslational modification, protein turnover, chaperones | 49 |
| Energy production and conversion | 72 |
| Carbohydrate transport and metabolism | 112 |
| Amino acid transport and metabolism | 136 |
| Nucleotide transport and metabolism | 82 |
| Coenzyme transport and metabolism | 78 |
| Lipid transport and metabolism | 43 |
| Inorganic ion transport and metabolism | 71 |
| Secondary metabolites biosynthesis, transport and catabolism | 17 |
| General function prediction only | 197 |
| Function unknown | 469 |

Example 7. Confirmation of Changes in Genes Involved in Circadian Rhythm

In the experiment performed in Example 4, the small intestine of the mice of each experimental group was obtained and mRNA was extracted therefrom using the RNA-seq technique, after which changes in the expression of genes involved in circadian rhythm were measured using the Novaseq platform by Macrogen Co. Ltd.

Figure 4A:
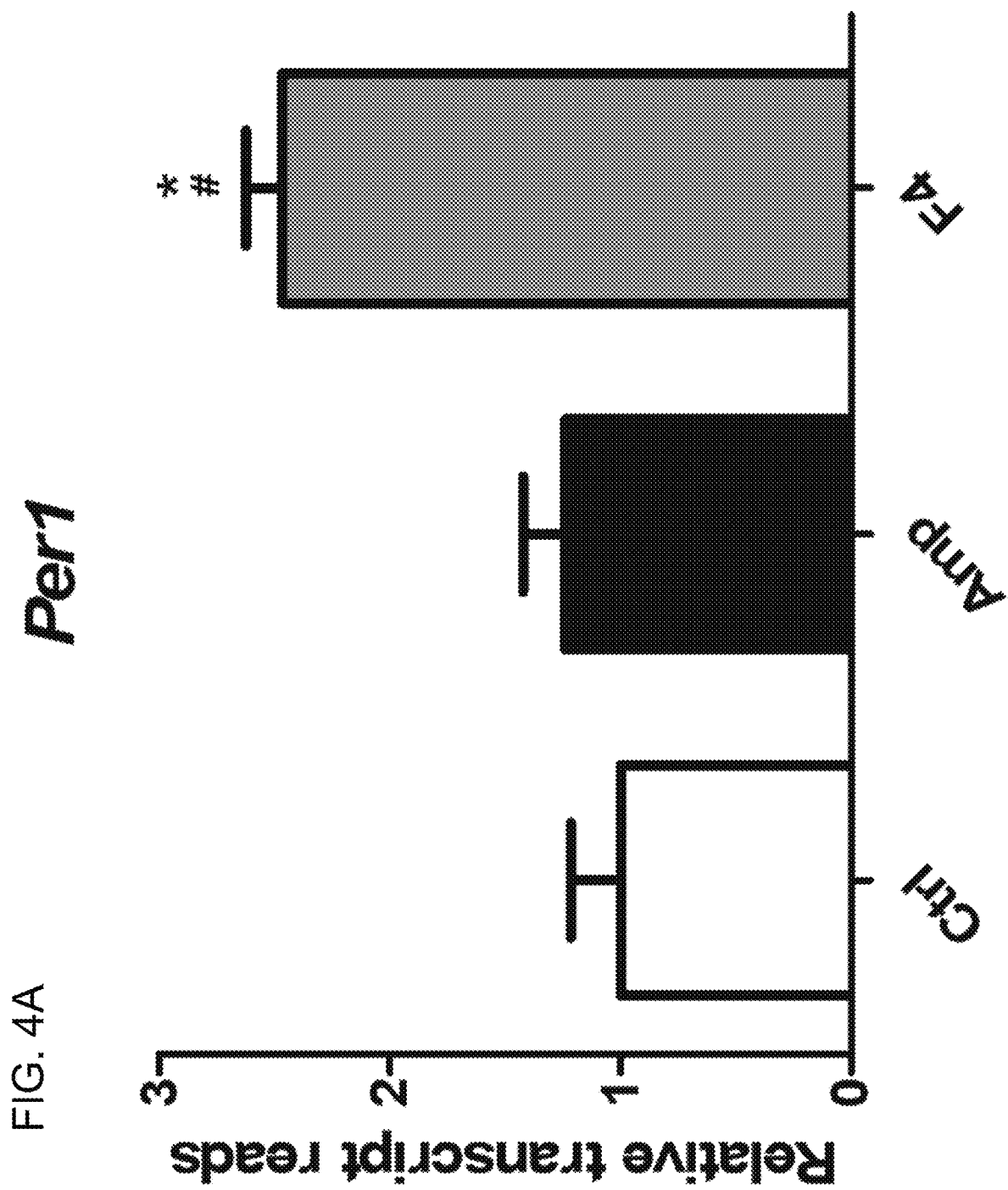
FIGS. 4A, 4B and 4C show the results of confirmation of changes in Per1 (NM_001159367.2), Per2 (NM_011066.3), and Per3 (NM_001289877.1), which are genes involved in the circadian rhythm of mice, depending on the ingestion of *Lactobacillus reuteri* ATG-F4 lactic-acid bacteria.
Figure 4B:
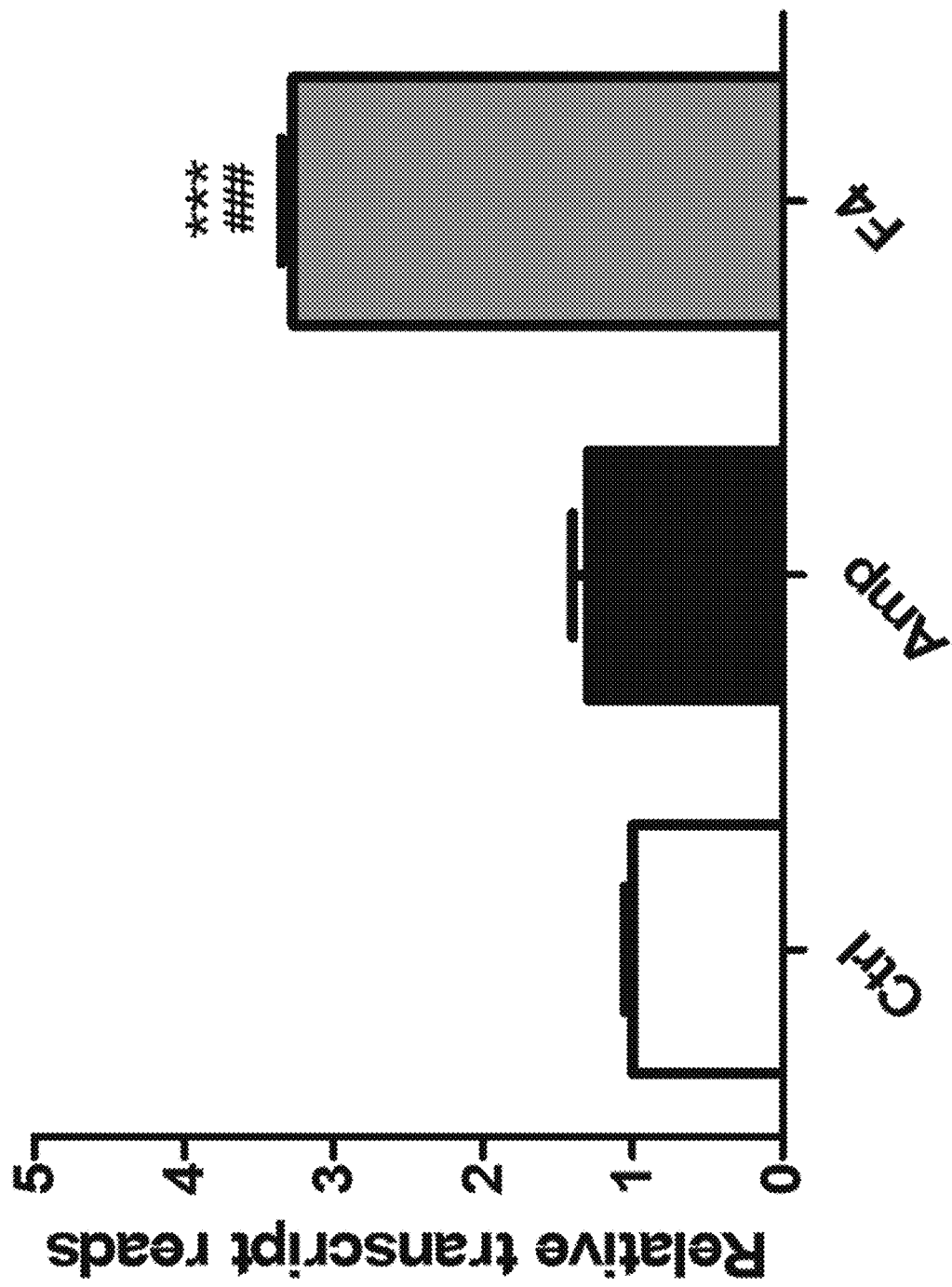
Figure 4C:
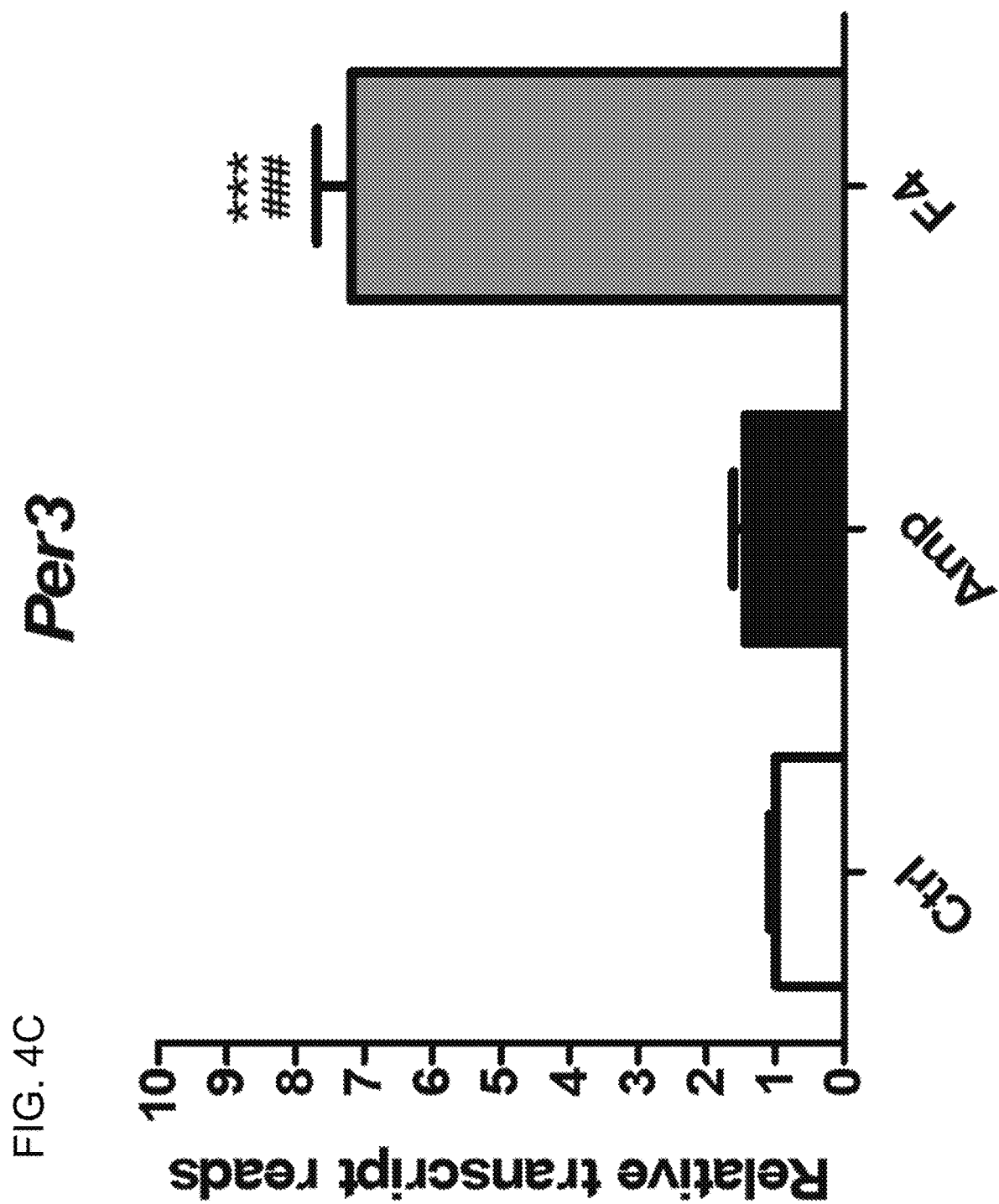

As shown in FIGS. 4A, 4B and 4C, Per1 (NM_001159367.2), Per2 (NM_011066.3), and Per3 (NM_001289877.1), which are genes involved in circadian rhythm, were significantly upregulated in F4 lactic-acid bacteria compared to the control (Ctrl) and the ampicillin-treated group (Amp).

It has been reported for these genes that circadian rhythm has various psychological effects on depression, autism, and Parkinson's disease in relation to Per1 (NM_002616.3), Per2 (NM_022817.3), and Per3 (NM_001289861.1) in humans (Nievergelt et al., 2006; Partonen et al., 2007; Lauretti et al., 2017), and furthermore, it has also been reported that circadian rhythm is associated with mood disorders encompassing various mental disorders in relation to dopamine production (Radwan et al., 2018).

In conclusion, it can be inferred that the circadian rhythm is strengthened by F4 lactic-acid bacteria and that the production of dopamine is increased in connection therewith, indicating that F4 lactic-acid bacteria can be ultimately applied to cognitive and neurological diseases.

Through the experiments of Examples 1 to 7 as described above, the *Lactobacillus reuteri* ATG-F4 lactic-acid bacteria according to the present disclosure as psychobiotics are characterized by having 1) an anti-inflammatory effect, 2) an effect of increasing the amount of dopamine in the blood, and 3) increased healthy gut microbiota. The anti-inflammatory effect is exhibited systemically, and particularly plays a role in preventing the increased adherence of the digestive organs and the absorption of toxic substances in the body and also in manifesting a systemic effect, thus making it possible to suppress the overactivity of immune cells related to neurons (Fung et al., 2017). Dopamine, which is an important neurotransmitter for emotional development, affects other neurotransmitters related to happiness and quality of life, such as serotonin, oxytocin, and the like, and is associated with stress resistance (Baskerville and Douglas, 2010) and also with attention deficit hyperactivity disorder (ADHD) (Ayano, 2016).

In this regard, there is a view from academia that the direct and indirect positive effects of the relationship between neurotransmitters such as dopamine and serotonin and gut microorganisms have evolved into a state of symbiosis (Johnson and Foster, 2018). In changes in gut microbiota, the amount of Bacteroidetes was remarkably increased, which is considered a healthy change in gut microbiota. For the decrease in the amount of Bacteroidetes and the decreased Bacteroidetes/Firmicute ratio in individuals suffering from mental illness, it has been reported that changes in gut microbiota are closely related to the onset of mental disorders such as autism, depression and the like (Barrett et al., 2013; Desbonnet et al., 2014; Dinan and Cryan, 2015; Fung et al., 2017).

Therefore, the *Lactobacillus reuteri* ATG-F4 lactic-acid bacteria of the present disclosure are deemed to exhibit the properties of psychobiotics through the three effects described above. In particular, increasing dopamine secretion in vivo by feeding with *Lactobacillus reuteri* ATG-F4 lactic-acid bacteria is considered to be a remarkable finding.

Formulation Example 1. Preparation of Food

Formulation Example 1-1. Preparation of Cooking Seasoning

A cooking seasoning for health improvement was manufactured by adding 1 wt % of the *Lactobacillus reuteri* ATG-F4 strain of the present disclosure to a cooking seasoning.

Formulation Example 1-2. Preparation of Wheat Flour Food

Food for health improvement was manufactured by adding 0.1 wt % of the *Lactobacillus reuteri* ATG-F4 strain of the present disclosure to wheat flour to afford a mixture, which was then made into breads, cakes, cookies, crackers and noodles.

Formulation Example 1-3. Preparation of Dairy Products

Various dairy products such as butter and ice cream were manufactured using milk containing 0.1 wt % of the *Lactobacillus reuteri* ATG-F4 strain of the present disclosure.

Formulation Example 1-4. Preparation of Vegetable Juice

A vegetable juice for health improvement was manufactured by adding 0.5 g of the *Lactobacillus reuteri* ATG-F4 strain of the present disclosure to 1,000 ml of tomato juice or carrot juice

Formulation Example 1-5. Preparation of Fruit Juice

A fruit juice for health improvement was manufactured by adding 0.1 g of the *Lactobacillus reuteri* ATG-F4 strain of the present disclosure to 1,000 ml of apple juice or grape juice.

Formulation Example 2. Preparation of Pharmaceutical Composition

A capsule formulation was manufactured by mixing 0.1 g of a lyophilized powder of the *Lactobacillus reuteri* ATG-F4 strain of the present disclosure with 0.5 g of lactose to afford a mixture, which was then placed in a collagen capsule.

DEPOSITARY AUTHORITY

Name of Depositary Authority: Korean Collection for Type Cultures
Accession number: KCTC13717BP
Accession date: 20181115

The invention claimed is:

1. A method for preventing or treating mental illness comprising administering a composition comprising a *Lactobacillus reuteri* ATG-F4 strain (Accession number: KCTC13717BP) or a culture thereof to a subject in need thereof,
wherein the mental illness is selected from the group consisting of attention deficit hyperactivity disorder, memory disorder, bipolar disorder and Parkinson's disease.

2. The method of claim 1, wherein the strain has anti-inflammatory efficacy.

3. The method of claim 1, wherein the strain has function of enhancing dopamine secretion.

* * * * *

SEQUENCE LISTING

<160> NUMBER OF SEQ ID NOS: 5

<210> SEQ ID NO 1
<211> LENGTH: 1523
<212> TYPE: DNA
<213> ORGANISM: Unknown
<220> FEATURE:
<223> OTHER INFORMATION: Lactobacillus reuteri

<400> SEQUENCE: 1

```
tcaggatgaa cgccggcggt gtgcctaata catgcaagtc gtacgcactg gcccaactga        60
ttgatggtgc ttgcacctga ttgacgatgg atcaccagtg agtggcggac gggtgagtaa       120
cacgtaggta acctgccccg gagcggggga taacatttgg aaacagatgc taataccgca       180
taacaacaaa agccgcatgg cttttgtttg aaagatggct ttggctatca ctctgggatg       240
gacctgcggt gcattagcta gttggtaagg taacggctta ccaaggcgat gatgcatagc       300
cgagttgaga gactgatcgg ccacaatgga actgagacac ggtccatact cctacgggag       360
gcagcagtag ggaatcttcc acaatgggcg caagcctgat ggagcaacac cgcgtgagtg       420
aagaagggtt tcggctcgta aagctctgtt gttggagaag aacgtgcgtg agagtaactg       480
ttcacgcagt gacggtatcc aaccagaaag tcacggctaa ctacgtgcca gcagccgcgg       540
taatacgtag gtggcaagcg ttatccggat ttattgggcg taaagcgagc gcaggcggtt       600
gcttaggtct gatgtgaaag ccttcggctt aaccgaagaa gtgcatcgga accgggcga       660
cttgagtgca gaagaggaca gtggaactcc atgtgtagcg gtggaatgcg tagatatatg       720
gaagaacacc agtggcgaag gcggctgtct ggtctgcaac tgacgctgag gctcgaaagc       780
atgggtagcg aacaggatta gataccctgg tagtccatgc cgtaaacgat gagtgctagg       840
tgttggaggg tttccgccct tcagtgccgg agctaacgca ttaagcactc cgcctgggga       900
gtacgaccgc aaggttgaaa ctcaaaggaa ttgacggggg cccgcacaag cggtggagca       960
tgtggtttaa ttcgaagcta cgcgaagaac cttaccaggt cttgacatct gcgctaacc      1020
ttagagataa ggcgttccct cggggacgc aatgacaggt ggtgcatggt cgtcgtcagc      1080
tcgtgtcgtg agatgttggg ttaagtcccg caacgagcgc aacccttgtt actagttgcc      1140
agcattgagt tgggcactct agtgagactg ccggtgacaa accggaggaa ggtggggacg      1200
acgtcagatc atcatgcccc ttatgacctg gctacacac gtgctacaat ggacggtaca      1260
acgagtcgca aactcgcgag agtaagctaa tctcttaaag ccgttctcag ttcggactgt      1320
aggctgcaac tcgcctacac gaagtcggaa tcgctagtaa tcgcggatca gcatgccgcg      1380
gtgaatacgt tcccgggcct tgtacacacc gcccgtcaca ccatgggagt tgtaacgcc      1440
caaagtcggt ggcctaacct ttatggaggg agccgcctaa ggcgggacag atgactgggg      1500
tgaagtcgta acaggaaacc ccg                                             1523
```

<210> SEQ ID NO 2
<211> LENGTH: 20
<212> TYPE: DNA
<213> ORGANISM: Unknown
<220> FEATURE:
<223> OTHER INFORMATION: 27F

<400> SEQUENCE: 2

```
agagtttgat cctggctcag                                                   20
```

<210> SEQ ID NO 3
<211> LENGTH: 19

```
<212> TYPE: DNA
<213> ORGANISM: Unknown
<220> FEATURE:
<223> OTHER INFORMATION: 518F

<400> SEQUENCE: 3
ccagcagccg cggtaatac                                          19

<210> SEQ ID NO 4
<211> LENGTH: 20
<212> TYPE: DNA
<213> ORGANISM: Unknown
<220> FEATURE:
<223> OTHER INFORMATION: 907R

<400> SEQUENCE: 4
ccgtcaattc mtttragttt                                         20

<210> SEQ ID NO 5
<211> LENGTH: 19
<212> TYPE: DNA
<213> ORGANISM: Unknown
<220> FEATURE:
<223> OTHER INFORMATION: 1492R

<400> SEQUENCE: 5
ggttaccttg ttacgactt                                          19
```